United States Patent
Zhao et al.

(10) Patent No.: US 10,278,615 B2
(45) Date of Patent: May 7, 2019

(54) SYSTEMS AND METHODS FOR REGISTRATION OF MULTIPLE VISION SYSTEMS

(71) Applicant: Intuitive Surgical Operations, Inc., Sunnyvale, CA (US)

(72) Inventors: Tao Zhao, Sunnyvale, CA (US); Prashant Chopra, Sunnyvale, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 163 days.

(21) Appl. No.: 13/964,704

(22) Filed: Aug. 12, 2013

(65) Prior Publication Data

US 2014/0051986 A1    Feb. 20, 2014

Related U.S. Application Data

(60) Provisional application No. 61/682,966, filed on Aug. 14, 2012.

(51) Int. Cl.
| | | |
|---|---|---|
| A61B 5/00 | (2006.01) | |
| A61B 5/06 | (2006.01) | |
| A61B 1/00 | (2006.01) | |
| A61B 34/20 | (2016.01) | |
| G06T 7/33 | (2017.01) | |

(52) U.S. Cl.
CPC .......... *A61B 5/066* (2013.01); *A61B 1/00009* (2013.01); *A61B 34/20* (2016.02); *G06T 7/33* (2017.01); *A61B 5/062* (2013.01); *A61B 2034/2065* (2016.02); *G06T 2207/10068* (2013.01); *G06T 2207/30021* (2013.01)

(58) Field of Classification Search
CPC ............ A61B 5/066; A61B 2019/5287; A61B 2019/5289; A61B 19/5244
USPC .......................................................... 600/424
See application file for complete search history.

(56) References Cited

U.S. PATENT DOCUMENTS

| | | |
|---|---|---|
| 5,495,540 A | 2/1996 | Frankot et al. |
| 6,380,732 B1 | 4/2002 | Gilboa |
| 6,389,187 B1 | 5/2002 | Greenaway et al. |

(Continued)

FOREIGN PATENT DOCUMENTS

| | | |
|---|---|---|
| CN | 1658789 A | 8/2005 |
| CN | 102186404 A | 9/2011 |

(Continued)

OTHER PUBLICATIONS

International Search Report and Written Opinion for Application No. PCT/US13/54555, dated Nov. 27, 2013, 14 pages.

(Continued)

*Primary Examiner* — Joel F Brutus (57) ABSTRACT

A method comprises generating a model of an anatomic region and receiving a true image from an endoscopic image capture probe positioned within the anatomic region. The method further comprises identifying a true fiducial region in the true image and identifying a plurality of virtual tissue structures in the model of the anatomic region. The method further comprises matching one of the plurality of the virtual tissue structures with the true fiducial region and determining a probe pose of the endoscopic image capture probe from the matched one of the plurality of virtual tissue structures.

21 Claims, 8 Drawing Sheets

(56) References Cited

U.S. PATENT DOCUMENTS

| | | | |
|---|---|---|---|
| 7,756,563 B2 | 7/2010 | Higgins et al. | |
| 7,889,905 B2 | 2/2011 | Higgins et al. | |
| 7,901,348 B2 | 3/2011 | Soper et al. | |
| 7,930,065 B2 | 4/2011 | Larkin et al. | |
| 2004/0034300 A1 | 2/2004 | Verard et al. | |
| 2004/0249267 A1 | 12/2004 | Gilboa | |
| 2006/0013523 A1 | 1/2006 | Childers et al. | |
| 2006/0149134 A1* | 7/2006 | Soper | A61B 1/0008 600/182 |
| 2006/0184016 A1* | 8/2006 | Glossop | 600/434 |
| 2006/0281971 A1* | 12/2006 | Sauer | A61B 19/52 600/109 |
| 2007/0179496 A1* | 8/2007 | Swoyer et al. | 606/41 |
| 2007/0293721 A1 | 12/2007 | Gilboa | |
| 2008/0004633 A1* | 1/2008 | Arata | A61B 17/1764 606/130 |
| 2008/0207997 A1 | 8/2008 | Higgins et al. | |
| 2008/0212082 A1 | 9/2008 | Froggatt et al. | |
| 2009/0054729 A1 | 2/2009 | Mori et al. | |
| 2009/0161927 A1 | 6/2009 | Mori et al. | |
| 2009/0252395 A1 | 10/2009 | Chan et al. | |
| 2009/0268955 A1* | 10/2009 | Koolwal et al. | 382/128 |
| 2009/0292175 A1 | 11/2009 | Akimoto et al. | |
| 2010/0041949 A1* | 2/2010 | Tolkowsky | 600/109 |
| 2010/0239147 A1* | 9/2010 | Vitanovski | G06K 9/4638 382/131 |
| 2010/0280365 A1 | 11/2010 | Higgins et al. | |
| 2011/0128352 A1 | 6/2011 | Higgins et al. | |
| 2011/0184238 A1* | 7/2011 | Higgins et al. | 600/117 |
| 2012/0289777 A1 | 11/2012 | Chopra et al. | |

FOREIGN PATENT DOCUMENTS

| | | |
|---|---|---|
| EP | 2423877 A1 | 2/2012 |
| JP | 2005131043 A | 5/2005 |
| JP | 2008541860 A | 11/2008 |
| JP | 2009279251 A | 12/2009 |
| JP | 2012024518 A | 2/2012 |
| WO | WO-2008095068 A1 | 8/2008 |
| WO | WO-2010078009 A1 | 7/2010 |
| WO | WO-2011086431 A1 | 7/2011 |
| WO | WO-2012035492 A1 | 3/2012 |
| WO | WO-2012095755 A1 | 7/2012 |

OTHER PUBLICATIONS

Soper T.D., et al., "In Vivo Validation of a Hybrid Tracking System for Navigation of an Ultrathin Bronchoscope within Peripheral Airways," IEEE Transactions on Biomedical Engineering, 2010, vol. 57 (3), pp. 736-745.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. EP13829698.3, dated Mar. 29, 2016, 11 pages.

Bricault L., et al., "Registration of Real and CT-derived Virtual Bronchoscopic Images to Assist Transbronchial Biopsy," IEEE Transactions on Medical Imaging, Oct. 1998, vol. 17 (5), pp. 703-714.

* cited by examiner

SYSTEMS AND METHODS FOR REGISTRATION OF MULTIPLE VISION SYSTEMS

This application claims the benefit of U.S. Provisional Application 61/682,966 filed Aug. 14, 2012, which is incorporated by reference herein in its entirety.

FIELD

The present disclosure is directed to systems and methods for navigating a patient anatomy to conduct a minimally invasive procedure, and more particularly to systems and methods for registering multiple vision systems for use in conducting a minimally invasive procedure.

BACKGROUND

Minimally invasive medical techniques are intended to reduce the amount of tissue that is damaged during interventional procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert interventional instruments (including surgical, diagnostic, therapeutic, or biopsy instruments) to reach a target tissue location. To reach the target tissue location, the minimally invasive interventional instruments may navigate natural or surgically created passageways in anatomical systems such as the lungs, the colon, the intestines, the kidneys, the heart, the circulatory system, or the like. Multiple systems may be used to assist the clinician in guiding the interventional instruments through the anatomical passageways. These systems include visualization systems that display to the clinician a view of the anatomical passageway from the viewpoint of the interventional instrument. Improved systems and methods are needed for utilizing multiple visualization systems to enhance clinician understanding of the location and pose of the interventional instrument.

SUMMARY

The embodiments of the invention are summarized by the claims that follow below.

In one embodiment, a method comprises generating a model of an anatomic region and receiving a true image from an endoscopic image capture probe positioned within the anatomic region. The method further comprises identifying a true fiducial region in the true image and identifying a plurality of virtual tissue structures in the model of the anatomic region. The method further comprises matching one of the plurality of the virtual tissue structures with the true fiducial region and determining a probe pose of the endoscopic image capture probe from the matched one of the plurality of virtual tissue structures.

In another embodiment, a medical system comprises a flexible catheter body, an image capture probe extending within the catheter body, and a memory storing anatomical data describing an anatomic region. The system further comprises a processor configured for generating a model of the anatomic region and receiving a true image from the image capture probe positioned within the anatomic region. The processor is further configured for identifying a true fiducial region in the true image and identifying a plurality of virtual tissue structures in the model of the anatomic region. The processor is further configured for matching one of the plurality of the virtual tissue structures with the true fiducial region and determining a probe pose of the image capture probe from the matched one of the plurality of virtual tissue structures.

A method of registering anatomical images, the method comprises generating a three dimensional model of an anatomic region and receiving a true image from an endoscopic image capture probe positioned within the anatomic region. The method further comprises identifying a true fiducial region in the true image and receiving position information from a position sensor identifying a subregion of the anatomic region where a tip of the probe is located. The method further comprises identifying a plurality of virtual tissue structures in the subregion, matching one of the plurality of the virtual tissue structures in the subregion with the true fiducial region, and determining a probe pose of the endoscopic image capture probe from the matched one of the plurality of virtual tissue structures in the subregion.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 3b is a representation of tissue structures extracted from the true image of FIG. 3a.

FIGS. 3c and 3d are hierarchical representations of the tissue structures extracted from the true image of FIG. 3a.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Figure 1:
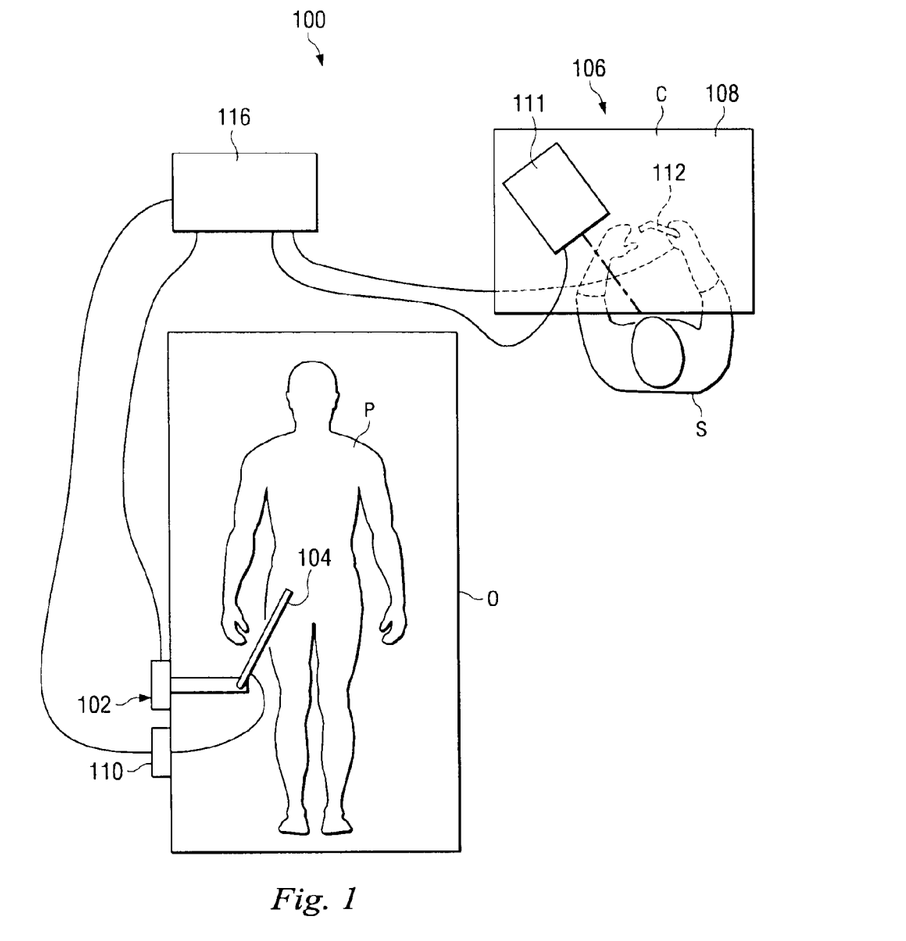
FIG. 1 is a robotic interventional system, in accordance with embodiments of the present disclosure.

Referring to FIG. 1 of the drawings, a robotic interventional system for use in, for example, surgical, diagnostic, therapeutic, or biopsy procedures, is generally indicated by the reference numeral 100. As shown in FIG. 1, the robotic system 100 generally includes an interventional manipulator assembly 102 for operating an interventional instrument 104 in performing various procedures on the patient P. The assembly 102 is mounted to or near an operating table O. A master assembly 106 allows the surgeon S to view the surgical site and to control the slave manipulator assembly 102.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assemblies 102. The control device(s) 112 may include any number of a variety of input devices, such as joysticks, trackballs, data gloves, trigger-guns, hand-operated controllers, voice recognition devices, body motion or presence sensors, or the like. In some embodiments, the control device(s) 112 will be provided with the same degrees of freedom as the associated interventional instruments 104 to provide the surgeon with telepresence, or the perception that the control device(s) 112 are integral with the instruments 104 so that the surgeon has a strong sense of directly controlling instruments 104. In other embodiments, the control device(s) 112 may have more or fewer degrees of freedom than the associated interventional instruments 104 and still provide the surgeon with telepresence. In some embodiments, the control device(s) 112 are manual input devices which move with six degrees of freedom, and which may also include an actuatable handle for actuating instruments (for example, for closing grasping jaws, applying an electrical potential to an electrode, delivering a medicinal treatment, or the like).

In alternative embodiments, the robotic system may include more than one slave manipulator assembly and/or more than one master assembly. The exact number of manipulator assemblies will depend on the surgical procedure and the space constraints within the operating room, among other factors. The master assemblies may be collocated, or they may be positioned in separate locations. Multiple master assemblies allow more than one operator to control one or more slave manipulator assemblies in various combinations.

A visualization system 110 may include an endoscope system such that a concurrent (real-time) image of the surgical site is provided to surgeon console C. The concurrent image may be, for example, a two- or three-dimensional image captured by an endoscopic probe positioned within the surgical site. In this embodiment, the visualization system 110 includes endoscopic components that may be integrally or removably coupled to the interventional instrument 104. In alternative embodiments, however, a separate endoscope attached to a separate manipulator assembly may be used to image the surgical site. Alternatively, a separate endoscope assembly may be directly operated by a user, without robotic control. The endoscope assembly may include active steering (e.g., via teleoperated steering wires) or passive steering (e.g., via guide wires or direct user guidance). The visualization system 110 may be implemented as hardware, firmware, software, or a combination thereof, which interacts with or is otherwise executed by one or more computer processors, which may include the processor(s) of a control system 116.

A display system 111 may display an image of the surgical site and interventional instruments captured by the visualization system 110. The display 111 and the master control device(s) 112 may be oriented such that the relative positions of the imaging device in the scope assembly and the interventional instruments are similar to the relative positions of the surgeon's eyes and hand(s) so the operator can manipulate the interventional instrument 104 and the master control device(s) 112 as if viewing the workspace in substantially true presence. True presence means that the displayed tissue image appears to an operator as if the operator was physically present at the imager location and directly viewing the tissue from the imager's perspective.

Alternatively or additionally, display system 111 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images.

In some embodiments, the display system 111 may display a virtual visualization image in which the actual location of the interventional instrument is registered (e.g., dynamically referenced) with preoperative or concurrent images to present the surgeon S with a virtual image of the internal surgical site at the location of the tip of the surgical instrument.

In other embodiments, the display system 111 may display a virtual visualization image in which the actual location of the interventional instrument is registered with prior images (including preoperatively recorded images) or concurrent images to present the surgeon S with a virtual image of an interventional instrument at the surgical site. An image of a portion of the interventional instrument may be superimposed on the virtual image to assist the surgeon controlling the interventional instrument.

As shown in FIG. 1, a control system 116 includes at least one processor (not shown), and typically a plurality of processors, for effecting control between the slave surgical manipulator assembly 102, the master assembly 106, the visualization system 110, and the display system 111. The control system 116 also includes programmed instructions (e.g., a computer-readable medium storing the instructions) to implement some or all of the methods described herein.

While control system 116 is shown as a single block in the simplified schematic of FIG. 1, the system may comprise a number of data processing circuits (e.g., on the slave surgical manipulator assembly 102 and/or on the master assembly 106), with at least a portion of the processing optionally being performed adjacent the slave surgical manipulator assembly, a portion being performed the master assembly, and the like. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 116 supports wireless communication protocols such as Bluetooth, IrDA, HomeRF, IEEE 802.11, DECT, and Wireless Telemetry.

In some embodiments, control system 116 may include one or more servo controllers to provide force and torque feedback from the interventional instruments 104 to one or more corresponding servomotors for the control device(s) 112. The servo controller(s) may also transmit signals instructing manipulator assembly 102 to move instruments which extend into an internal surgical site within the patient body via openings in the body. Any suitable conventional or specialized servo controller may be used. A servo controller may be separate from, or integrated with, manipulator assembly 102. In some embodiments, the servo controller and manipulator assembly are provided as part of a robotic arm cart positioned adjacent to the patient's body.

Each manipulator assembly 102 supports a interventional instrument 104 and may comprise a kinematic structure of one or more non-servo controlled links (e.g., one or more links that may be manually positioned and locked in place, generally referred to as a set-up structure) and a robotic manipulator. The robotic manipulator assembly 102 is driven by a plurality of actuators (e.g., motors). These motors actively move the robotic manipulators in response to commands from the control system 116. The motors are further coupled to the interventional instrument so as to advance the interventional instrument into a naturally or surgically created anatomical orifice and to move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

Figure 2:
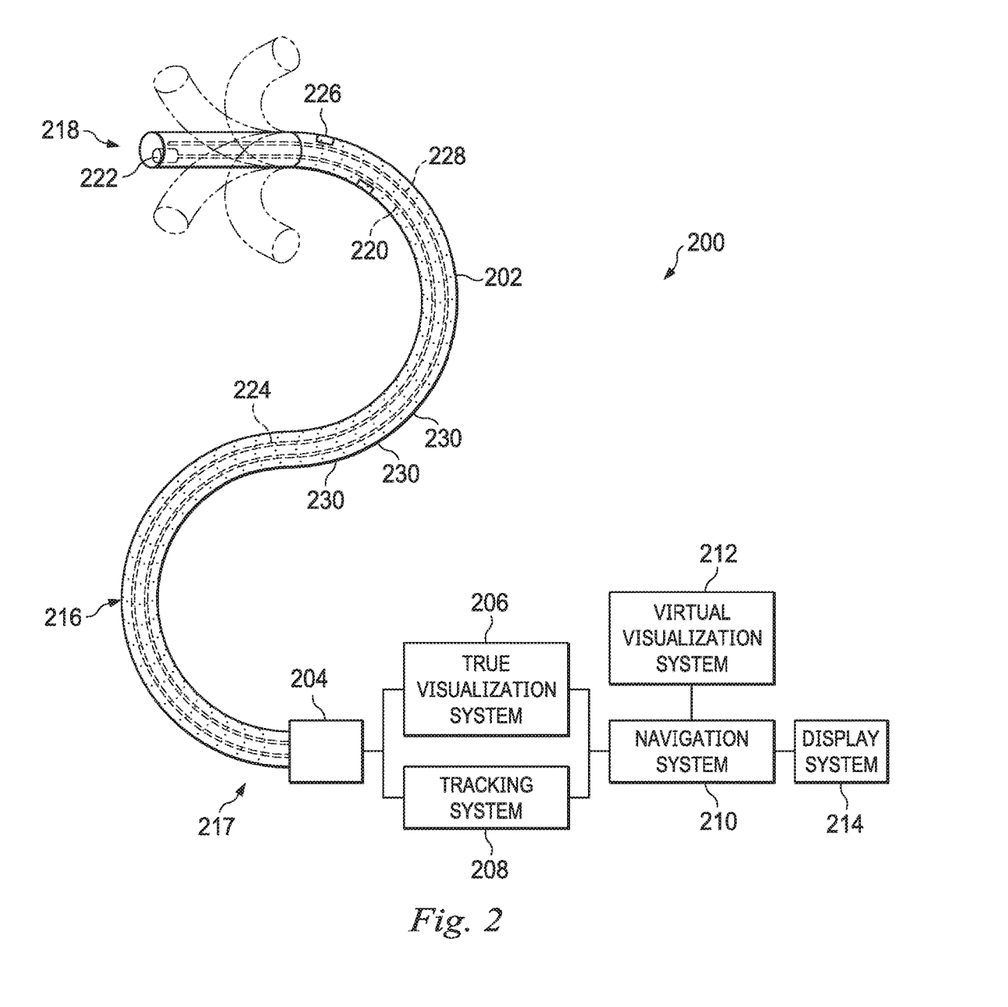
FIG. 2 illustrates an interventional instrument system utilizing aspects of the present disclosure.

FIG. 2 illustrates a minimally invasive system 200 utilizing aspects of the present disclosure. The system 200 may be incorporated into a robotic interventional system, such as system 100. Alternatively, the system 200 may be used for non-robotic exploratory procedures or in procedures involving traditional manually operated interventional instruments, such as laparoscopic instruments. The system 200 includes a catheter system 202 (e.g., part of the instrument 104) coupled by an interface unit 204 to a true visualization system 206 and a tracking system 208. A navigation system 210 (e.g., part of the control system 116) processes information from the true visualization system 206, the tracking system 208, and a virtual visualization system 212 for display on a display system 214 (e.g., part of the display system 111). The system 200 may further include optional operation and support systems (not shown) such as illumination systems, steering control systems, irrigation systems, and/or suction systems.

The catheter system 202 includes an elongated flexible body 216 having a proximal end 217 and a distal end 218. In one embodiment, the flexible body 216 has an approximately 3 mm outer diameter. Other flexible body outer diameters may be larger or smaller. The flexible body 216 houses an image capture probe 220. The image capture probe 220 includes a tip portion with a stereoscopic or monoscopic camera 222 disposed near the distal end 218 of the flexible body 216 for capturing images (including video images) that are transmitted to and processed by the true visualization system 206. The image capture probe 220 also includes a cable 224 coupled to the camera for transmitting the captured image data to the true visualization system 206. Alternatively, the image capture instrument may be a fiber-optic bundle, such as a fiberscope, that couples to the imaging system. The image capture instrument may be single or multi-spectral, for example capturing image data in the visible spectrum, or capturing image data in the visible and infrared or ultraviolet spectrums.

The body 216 houses also cables, linkages, or other steering controls (not shown) that extend between the interface 204 and the tip distal end 218 to controllably bend or turn the distal end 218 as shown for example by the dotted line versions of the distal end. The catheter system may be steerable or, alternatively, may be non-steerable with no integrated mechanism for operator control of the instrument bending. The flexible body 214 may further house control mechanisms (not shown) for operating a surgical end effector or another working distal part that is manipulable for a medical function, e.g., for effecting a predetermined treatment of a target tissue. For instance, some end effectors have a single working member such as a scalpel, a blade, an optical fiber, or an electrode. Other end effectors may include pair or plurality of working members such as forceps, graspers, scissors, or clip appliers, for example. Examples of electrically activated end effectors include electrosurgical electrodes, transducers, sensors, and the like. Also or alternatively, the flexible body 216 can define one or more lumens through which interventional instruments can be deployed and used at a target surgical location.

The catheter system 202 optionally includes a position sensor system 226 (e.g., an electromagnetic (EM) sensor system) and a shape sensor system 228 for determining the position, orientation, speed, pose, and/or shape of the distal end 218 and of one or more segments 230 along the body 216. The entire length of the body 216, between the distal end 218 and the proximal end 217 may be effectively divided into the segments 230. The position sensor system 226 and the shape sensor system 228 interface with the tracking system 208. The tracking system 208 may be implemented as hardware, firmware, software or a combination thereof which interact with or are otherwise executed by one or more computer processors, which may include the processors of a control system 116. Additionally or alternatively, a position sensor system may be coupled to the probe 220. For example a five degree of freedom sensor may be coupled to the probe 220 near the distal tip while a larger six degree of freedom sensor may be coupled to the catheter at a more proximal location.

The position sensor system 226 may be an EM sensor system that includes one or more conductive coils that may be subjected to an externally generated electromagnetic field. Each coil of the EM sensor system 226 then produces an induced electrical signal having characteristics that depend on the position and orientation of the coil relative to the externally generated electromagnetic field. In one embodiment, the EM sensor system may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The shape sensor system 228 includes an optical fiber aligned with the flexible body 216 (e.g., provided within an interior channel (not shown) or mounted externally). The tracking system 208 may be coupled to a proximal end of the optical fiber. In one embodiment, the optical fiber has a diameter of approximately 200 μm. In other embodiments, the dimensions may be larger or smaller.

The optical fiber of the shape sensor system 228 forms a fiber optic bend sensor for determining the shape of the catheter system 202. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional patent application Ser. No. 12/047,056, filed on Aug. 10, 2010, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the catheter may be determined using other techniques. For example, if the history of the catheter's distal tip pose is stored for an interval of time that is smaller than the period for refreshing the navigation display or for alternating motion (e.g., inhalation and exhalation), the pose history can be used to reconstruct the shape of the device over the interval of time. As another example, historical pose, position, or orientation data may be stored for a known point of an instrument along a cycle of alternating motion, such as breathing. This stored data may be used to develop shape information about the catheter. Alternatively, a series of positional sensors, such as EM sensors, positioned along the catheter can be used for shape sensing. Alternatively, a history of data from a positional sensor, such as an EM sensor, on the instrument during a procedure may be used to represent the shape of the instrument, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber is used to monitor the shape of at least a portion of the catheter system 202. More specifically, light passing through the optical fiber is processed by the tracking system 208 for detecting the shape of the catheter system 202 and for utilizing that information to assist in surgical procedures. The tracking system 208 may include a detection system for generating and detecting the light used for determining the shape of the catheter system 202. This information, in turn, in can be used to determine other related variables, such as velocity and acceleration of the parts of an interventional instrument. By obtaining accurate measurements of one or more of these variables in real time, the controller can improve the accuracy of the robotic interventional system and compensate for errors introduced in driving the component parts. The sensing may be limited only to the degrees of freedom that are actuated by the robotic system, or may be applied to both passive (e.g., unactuated bending of the rigid members between joints) and active (e.g., actuated movement of the instrument) degrees of freedom.

As previously described, the true visualization system 206 processes real-time, true images received from the probe 220. The true visualization system 206 provides valuable information to the clinician about the current environment of the tip of the probe but provides little directional guidance for navigating the catheter to a specific target location. Furthermore, mucous, blood, and other bodily matter becomes adhered to the probe, causing obstruction of the received true images.

The virtual visualization system 212 provides additional navigation assistance. Virtual navigation using the virtual visualization system is based upon reference to an acquired dataset associated with the three dimensional structure of the anatomical passageways. More specifically, the virtual visualization system 212 processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or during a clinical procedure. In an alternative embodiment, a virtual visualization system may use standard models (i.e., not patient specific) or hybrids of a standard model and patient specific data. The model and any virtual images generated by the model may represent the static posture of a deformable anatomic region during one or more phases of motion (e.g., during an inspiration/expiration cycle of a lung).

During a virtual navigation procedure, the sensor systems may be used to compute an approximate location of the instrument with respect to the patient anatomy. The location can be tracked to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

Often, however, the use of sensor systems alone to register the tip of the probe with a virtual image from the virtual visualization system are not entirely adequate. For example, sensor systems may provide insufficient information about the position and orientation of the tip of the probe. This may cause the virtual visualization system incorrectly register the virtual image with the true pose of the probe, potentially resulting in an inaccurate placement of the probe within the virtual environment (e.g., showing the probe in the wrong branch of the airway tree), depicting a virtual image with an inaccurate view angle (e.g., a roll angle in the virtual image that does not correspond to the real-time true image received from the true visualization system), and/or various other registration mismatch-related effects.

In embodiments of the present disclosure, information from the true visualization system 206 and the virtual visualization system 212 are processed by the navigation system 210, optionally with sensor information from the tracking system 208, to generate a virtual visualization image that is accurately registered, both in position and orientation, with the true visualization image. In order to achieve an accurate registration of the virtual image to the true image, common features and structures are identified and associated in both the true image and the virtual image. Accurate registration of the two images may be useful to the clinician in navigating the catheter to a specific target location because the registration conveys information about the true position and orientation of the tip of the probe. The clinician is, thus, less likely to guide the catheter to unintended locations, minimizing the need for time-consuming and potentially injurious backtracking.

Figure 3A:
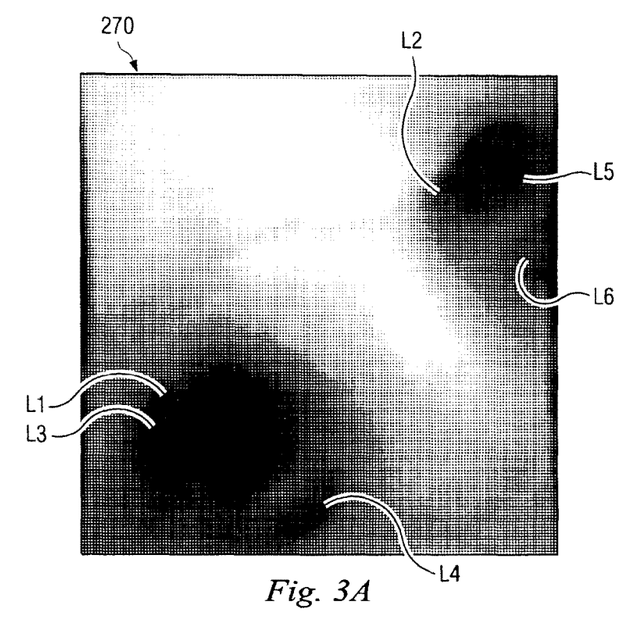
FIG. 3a is a sample true image from a visualization instrument within a lung.
Figure 3B:
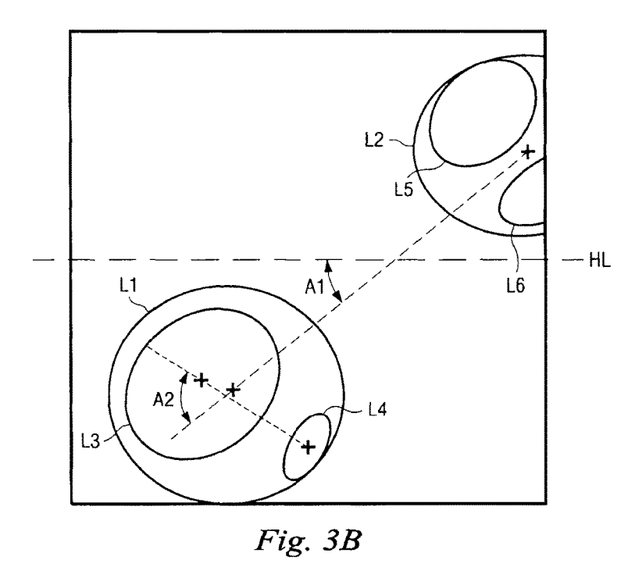

FIG. 3a shows a sample true image 270 of a bronchial passageway, captured, for example, by true visualization system 206. From true image 270, tissue structures (e.g., lumens L1-L6 and associated bifurcations) as depicted in FIG. 3b, along with structural aspects (e.g., location, relative positions, dimensions, contours, and shapes of the lumens) can be identified using any technique such as maximally stable extremal regions (MSER) analysis or other blob extraction techniques. Although reference will be made to anatomical passageway bifurcations, the embodiments of this disclosure are not limited to the junction of two passageways. It is understood that the systems and methods of this disclosure are applicable to any furcation with two or more branches or to any other identifiable tissue structure. Each natural tissue structures (e.g., lumens L1-L6 and associated bifurcations or other identifiable tissue structures) may be used as a fiducial region, providing a natural reference structure for registering to a virtual image.

For example, as shown in FIG. 3b, the relative sizes and shapes of lumens L1-L6 are indicated, along with the orientations of the bifurcation formed by lumen pair L1 and L2 relative to the horizontal axis HL of true image 270 (i.e., angle A1), and relative to the bifurcation formed by lumen pair L3 and L4 (i.e., angle A2). Various other structural aspects can be extracted from true image 270. Note that in various embodiments, a graphical representation of the detected tissue structures such as depicted in FIG. 3b may not be rendered for display, and in various other embodiments, the graphical representation may be overlaid onto true image 270.

Figure 3C:
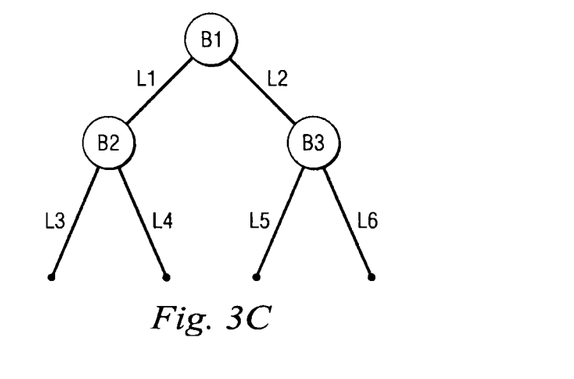

The identified fiducial region including the tissue structure(s) in true image 270 can also be characterized according to physical arrangement or hierarchy for more efficient analysis. For example, as shown in FIG. 3c, lumens L1-L6 can be organized into a tree structure representative of the anatomy shown in true image 270. Thus, lumens L1 and L2 branch from an initial bifurcation B1. Next, because lumens L3 and L4 are detected within lumen L1, FIG. 3c shows lumens B3 and B4 branching at a bifurcation B2 downstream from bifurcation B1. Likewise, lumens L5 and L6 branch at a bifurcation B3 downstream from bifurcation B1.

Figure 3D:
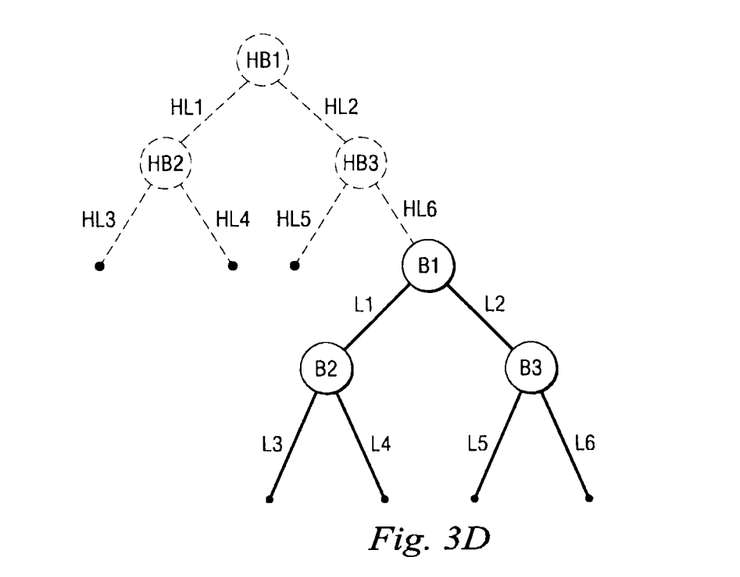

Note that although a node-branch stick figure diagram is depicted in FIG. 3c for exemplary purposes, the analytic representation of the tissue structures extracted from true image 270 can take any graphical, numeric, symbolic, and/or data library format. Note further that in some embodiments, a history of extracted lumens can be maintained to provide additional information for determining the location of the probe tip. For example, FIG. 3d shows the tree structure of FIG. 3c supplemented with lumens HL1-HL6 and bifurcations HB1-HB3 extracted from previous true images captured by the probe/visualization system as the patient anatomy is traversed.

Figure 3E:
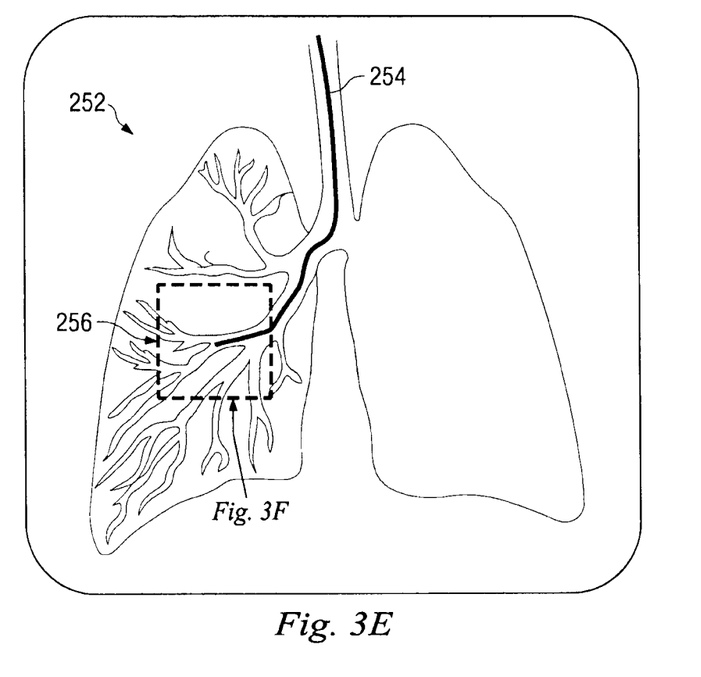
FIG. 3e is a tracking image depicting a lung within which a minimally invasive instrument is inserted.

In conjunction with the tissue structure identification described above (either concurrently, prior to, and/or after), a search space of potentially matching model tissue structures is defined from within the model of the target anatomy. For example, FIG. 3e shows an exemplary tracking image 251 depicting a two-dimensional view of a patient lung model 252 initially registered with an image 254 of a minimally invasive instrument (e.g., the catheter system 202). The tracking image 251 may be generated by the virtual visualization system (e.g., 212). This initial registration of the image 254 of the instrument 202 can be based upon a position sensor, such as an EM sensor, and/or any other indirect indication of position (e.g., kinematic modeling, shape sensing, RF tracking, and/or path history, among others).

All these approaches, however, will be subject to inaccuracies due to measurement precision limits and anatomic movement (e.g., patient breathing or tissue deformation in response to surgical instrumentation). For example, the positional information provided by an EM sensor may be accurate to approximately +/−3 mm with respect to the lung 252, using reference fiducials on the chest. When motion of the lungs is considered, the error may increase to approximately +/−10 mm or more. These errors may cause the image 254 of the instrument to become registered to the wrong airway of the lung 252.

Figure 3F:
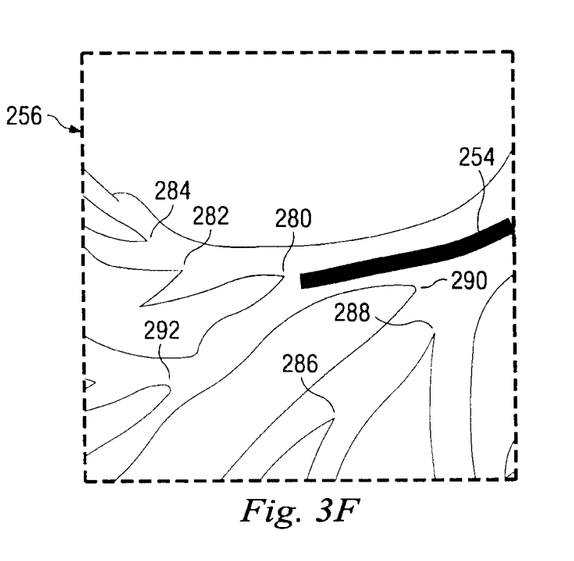
FIG. 3f is an enlarged view of a subregion of the tracking image of FIG. 3e.

To overcome this registration uncertainty, the tissue structures extracted from true image 270 can be compared potentially corresponding tissue structures from the pre-operative model of the anatomy to identify the best match between the model and the captured image. In some embodiments, the position of the tip of the probe can be estimated—e.g., using information from the position sensor system 226. As shown in FIG. 3e, the position of the tip of the probe 220 within the lung model 252 is estimated to be within a subregion 256, a detail view of which is shown in FIG. 3f.

Subregion 256 can be defined as any region within lung model 252 corresponding to the potential positions of the tip of probe 220 within the actual lung anatomy. For example, in some embodiments, subregion 256 can represent at least the maximum positional variation that can be expected from a stackup of sensor tolerance(s), anatomic motion/deformation, and/or any other sources of uncertainty associated with the positioning of the tip of probe 220 (note that the stackup can define the minimum boundaries of subregion 256, and in some embodiments, the actual boundaries of subregion 256 may exceed those minimum boundaries). In various other embodiments, subregion 256 can represent the universe of possible tissue structures (e.g., bifurcations) associated with the tip of probe 220, based on historical path analysis (i.e., keeping track of all bifurcations encountered as probe 220 is advanced to determine which bifurcation(s) could be encountered in sequence). These and other techniques for defining reduced space subregion 256 can be used individually or in combination.

Model tissue structures potentially corresponding to the tissue structures extracted from true image 270 (as described above) can then be extracted from model 252 from within subregion 256. The definition of subregion 256 can therefore significantly reduce the computational requirements of this model tissue structure extraction. For example, rather than extracting every bifurcation from lung model 252, only those bifurcations 280-292 shown in FIG. 3e need be extracted. These candidate tissue structures (e.g., bifurcations 280-292) can then be compared against the true image tissue structures (e.g., bifurcation B1).

In some embodiments, computational efficiency can be further enhanced by performing an initial "rough" matching of candidate tissue structures from the reduced space subregion against the true image tissue structures to filter out clearly non-matching candidates. This rough matching can be performed using structural aspects readily discernable from the true image and the model. As noted above, within the lung, such structural aspects can include location, relative positions, dimensions, contours, and/or shapes of the lumens, among others.

For example, as shown in FIGS. 3a and 3b, bifurcations (B2 and B3) are visible in both lumens (L1 and L2, respectively) of bifurcation B1. Referring next to the lung model subregion 256 shown in FIG. 3e, it can be determined that this condition of a visible downstream bifurcation in each lumen of bifurcation B1 cannot be met by model bifurcation 282, which only exhibits a downstream bifurcation in one of its branches. Model bifurcation 282 can therefore be eliminated from the list of candidate tissue structures. Model bifurcations 284 and 292 could potentially also be eliminated from the list of candidate tissue structures for similar reasons. In a similar manner, the list of candidate tissue structures can be further reduced via any other type of structural aspect-based filtering.

Each tissue structure that meets the structural aspect matching criteria described above can then be more precisely compared with the true image structure identified in the true image. Any technique can be used for determining the best match (similarity maximization) between the true image and the remaining candidate tissue structures, such as iterative rendering and image matching (analysis by synthesis), feature point cloud matching, and/or differential surface analysis.

For example, using analysis by synthesis, iterative renderings of each candidate tissue structure (e.g., model bifurcations 280, 286, 288, and 290) are generated, where each rendering is associated with the probe tip pose required to capture the view from the 3D anatomical model. The iterations are compared with the tissue structure extracted from the true image (e.g., bifurcation B1 extracted from true image 270), generating interim similarity measures from which an "optimum" similarity measure can be identified. This optimum similarity measure corresponds to the view of the candidate model tissue structure that best matches the true image tissue structure. From the optimum similarity measure values for each of the candidate model tissue structures, the greatest similarity measure can be selected, thereby indicating the candidate model tissue structure that corresponds to the true image tissue structure. The probe tip pose associated with that candidate model tissue structure and with the optimum similarity measure can then be used to register the anatomical model so that the true image matches best with a virtual image generated from the virtual camera probe tip. In an alternative embodiment, iterative rendering of the three dimensional anatomical model is used to compare to the true image without extracting tissue structures.

There are various ways in which the similarity measure can be computed, and the optimum measure found. In one embodiment, an optimization algorithm will drive the iterative renderings of each candidate tissue structure, and computation of similarity measure with true image. In another embodiment, the optimization algorithm drives a hierarchical image rendering and similarity computation framework where the resolution of images is increased in steps, to maximize the chances of stopping at the correct optimum, and to resist noise in similarity measure function space.

Figure 3G:
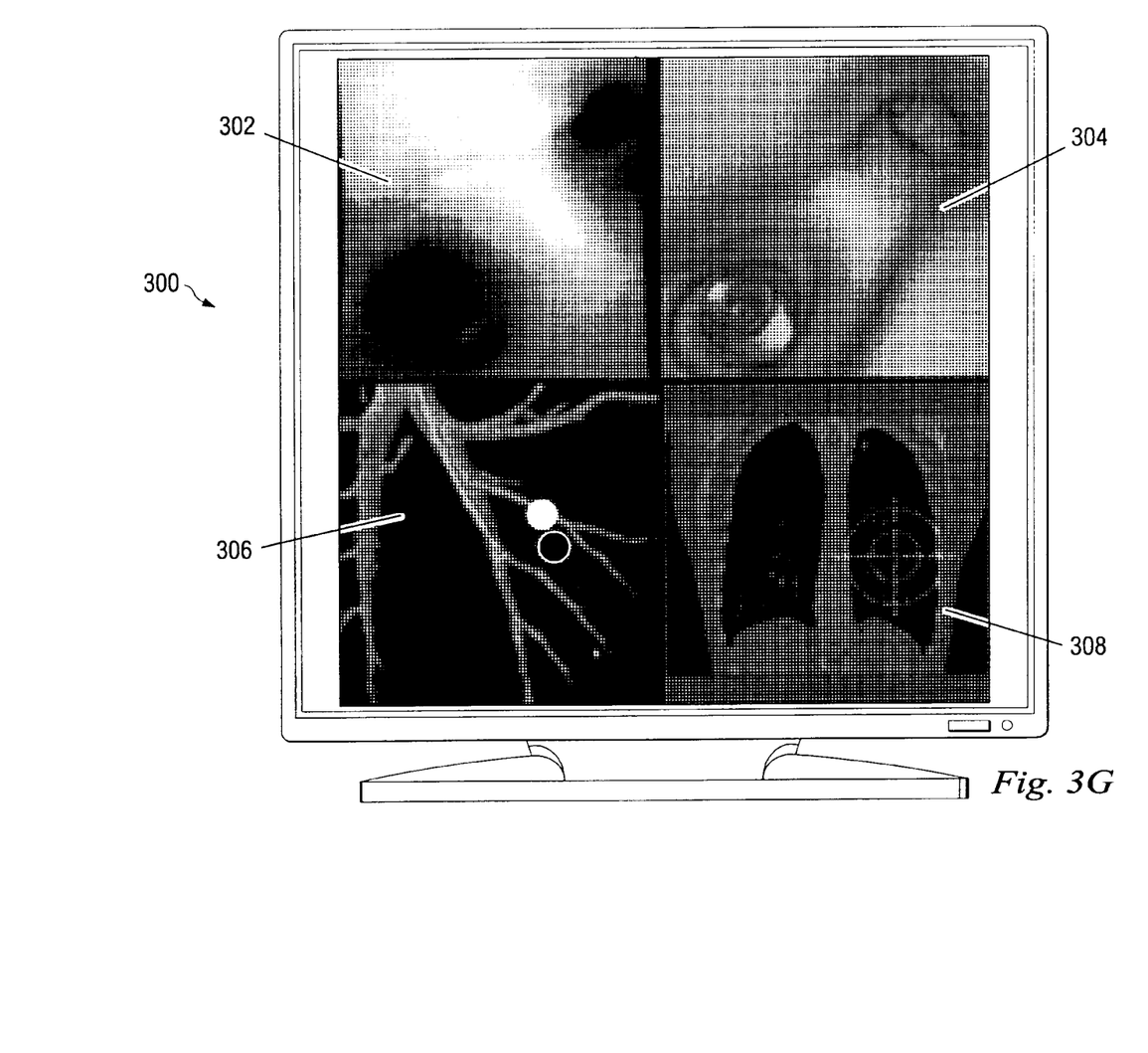
FIG. 3g is an exemplary display screen displaying a true image, a virtual image, a micro tracking image, and a macro tracking image.

The registration procedure can be used to transfer information associated with the three-dimensional anatomical model to the true images. This registration can be expressed graphically in various ways. For example, in FIG. 3g, a display 300 (e.g., in display system 111) provides a set of images. The true vision image 302 is shown with the registered virtual image 304 from the virtual model. In the registered images, the size of the lumens and the view angle (including the roll angle) of the virtual image 304 are aligned with the true image 302. A micro-tracking image 306 is shown with a marker 308 indicating the tip of the probe registered with a two-dimensional model of the lung. A macro tracking image 310 is shown with a marker 312 indicating the tip of the probe registered with a three dimensional model of the lung. Various other combinations of true image and virtual (model) views will be readily apparent.

In one embodiment, the registered virtual image (or features extracted from it e.g. contours, edges, feature points, anatomical labels) can be overlaid on the true image, with transparency that varies with the quality of match of the images. In another embodiment, the registered virtual image can be displayed as a picture-in-picture corner image on the true image. In another embodiment, navigation cues extracted from the registered tissue model (e.g. glyphs pointing in the planned direction, distance to the target, local diameter, a rear view camera view for retraction etc.) are displayed alongside or on the true vision image, in stereoscopic views. In yet another embodiment, the registered true image is displayed as a cross section on a 3D airway tree surface mesh or volume rendered display to signify the current location and orientation of the probe tip. In another embodiment, the overlays on the true images may be switched on and off in response to an automated trigger or a user command.

Figure 4A:
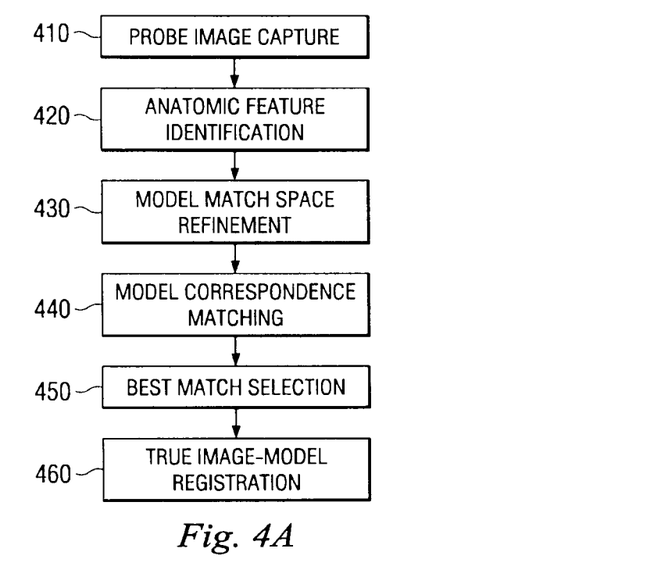
FIGS. 4a-4d are flowcharts illustrating a method for registering multiple visualization systems.

FIG. 4a shows a flow diagram of an anatomic model registration method, such as described above. In a PROBE IMAGE CAPTURE step 410, a true image (e.g., image 270) of the patient anatomy is captured by an imaging system, such as image capture probe 220 and associated true visualization system 206. Then, in an ANATOMIC FEATURE IDENTIFICATION step 420, relevant tissue structures are extracted from the true image, such as described with respect to FIGS. 3a and 3b. As part of step 420, structural aspects of the extracted tissue structures (e.g., location, relative positions, dimensions, contours, and shapes of the lumens) can be determined, as well as any other potentially identifying aspect.

Figure 4B:
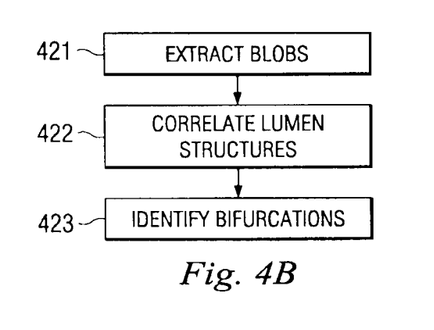

For example, FIG. 4b shows a flow diagram of an exemplary approach to the feature identification of step 420 that would be applicable for a branching anatomical structure, such as the airway tree in a lung or the arterial network in the kidney. In an EXTRACT BLOBS step 421, individual lumens can be detected in the true image (such as described with respect to FIGS. 3a and 3b), the sibling lumens (i.e., lumens forming a bifurcation) then be determined in a CORRELATE LUMEN STRUCTURES step 422. Finally, the detected bifurcations can be labeled (e.g., as shown in FIGS. 3c and 3d) and characterized (e.g., as shown in FIG. 3b) in an IDENTIFY BIFURCATIONS step 423.

Figure 4C:
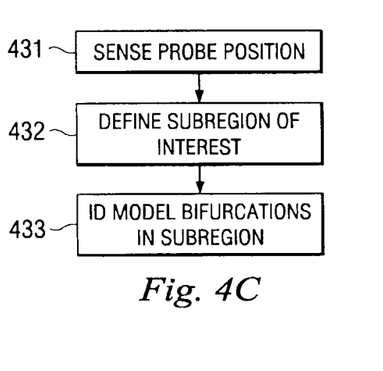

Returning to FIG. 4a, the initial number of potentially matching tissue structures in the anatomic model is defined in a MODEL MATCH SPACE REFINEMENT step 430. In one embodiment, this initial definition can be performed as indicated by the flow diagram in FIG. 4c. In a SENSE PROBE POSITION step 431, instrumentation (e.g., EM sensors, shape sensors, and/or other monitoring/tracking elements) is used to generate a position and/or orientation of the imaging system (probe) tip, and based on that sensed information, a portion of the anatomical model is designated as potentially containing the probe tip in a DEFINE SUB-REGION OF INTEREST step 432 (e.g., as described with respect to FIG. 3e). Then, the model tissue structures within that subregion of interest are identified in an ID MODEL BIFURCATIONS IN SUBREGION step 433 (e.g., as described with respect to FIG. 3f).

As noted above, reducing the search space in which the best match in the model for the true image can be found can significantly reduce the computational load associated with the technique. Returning to FIG. 4a, from the initial model candidate match space, unlikely candidates are filtered out in a MODEL CORRESPONDENCE MATCHING step 440, and the one of the remaining model candidates exhibiting the closest match to the true image tissue structure is selected in a BEST MATCH SELECTION step 450. By narrowing the candidate match space via steps 420, 430, and 440, the computational burden (and therefore the time) associated with the matching process can be significantly reduced over conventional brute force methods, while maintaining or even increasing match accuracy.

Figure 4D:
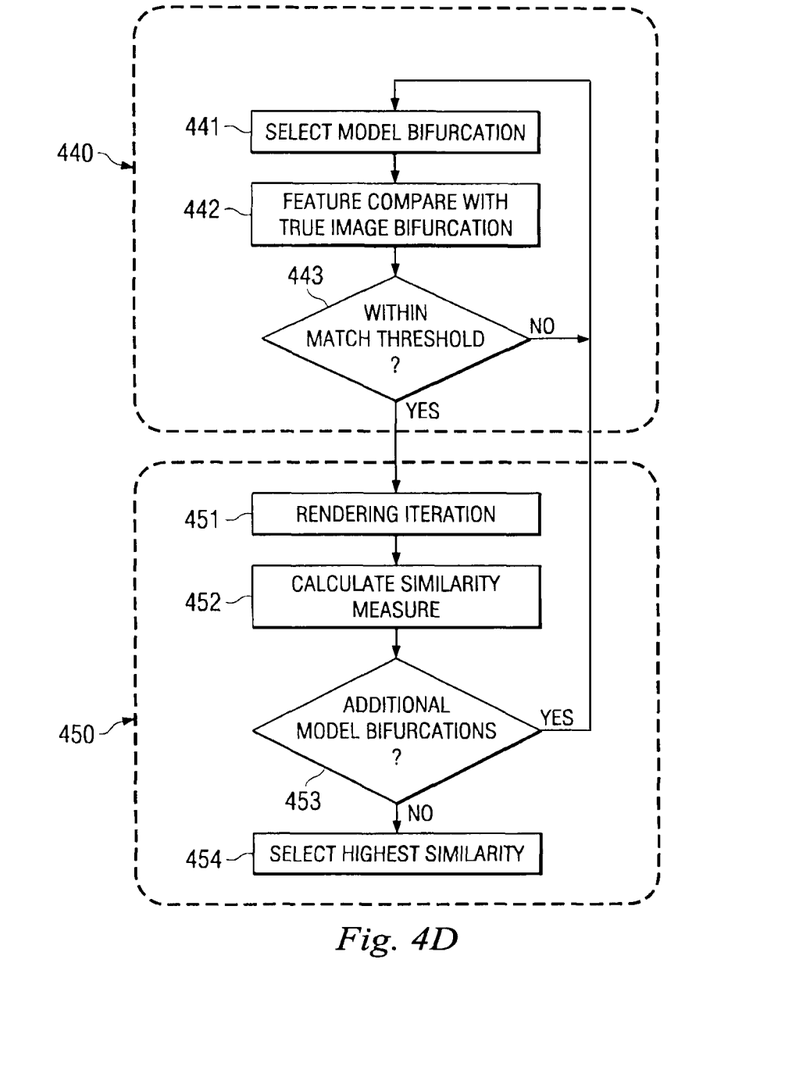

FIG. 4d shows a flowchart for an embodiment of steps 440 and 450 that would be applicable for a branching anatomical structure, such as the airway tree in a lung or the arterial network in the kidney. In a SELECT MODEL BIFURCATION step 441, one of the candidate model tissue structures (e.g., bifurcations 280-292 shown in FIG. 3e) is selected and the structural aspects (e.g., as described above with respect to FIG. 3b) of that candidate model tissue structure are compared with those of the true image tissue structure in a FEATURE COMPARE WITH TRUE IMAGE BIFURATION step 442. Then, in a WITHIN MATCH THRESHOLD step 443, if it is determined that no match is possible, the process loops back to step 441 and a different candidate model tissue structure is selected.

However, if the candidate model tissue structure remains a viable candidate based on the structural comparison, a more refined comparison is performed in a RENDERING ITERATION step 443. For exemplary purposes, an analysis by synthesis approach (as described above) is depicted in the flow chart, in which the candidate model tissue structure is iteratively modified (with each modification representing a different virtual camera pose) in a RENDERING ITERATION step 451 until a similarity measure for the rendering vis a vis the true image tissue structure is optimized in a CALCULATE SIMILARITY MEASURE step 452.

Then, in an ADDITIONAL MODEL BIFURCATIONS? step 453, the process loops back to step 441 if any unexamined candidate model tissue structures remain. Otherwise, the candidate model tissue structure associated with the greatest similarity measure is identified in a SELECT HIGHEST SIMILARITY step 454. Note that while a serial process is depicted for the candidate model tissue structures (i.e., steps 440 and 450 are performed on a single candidate tissue structure before moving on to the next candidate model tissue structure) for exemplary purposes, in various other embodiments steps 440 and 450 can be performed as batch processes (i.e., step 440 performed on all candidate model tissue structures, and then step 450 is performed on all the appropriate candidate model tissue structures identified in step 440).

Returning to FIG. 4a, the candidate model tissue structure identified in step 450 as having the highest similarity score is then used to register the true image and anatomic model in a TRUE IMAGE-MODEL REGISTRATION step 460. In one embodiment, a displayed virtual environment (e.g., virtual image 304 shown in FIG. 3g) can be generated from the rendering/pose information associated with the output of step 450 (e.g., the highest similarity measure rendering identified in step 454). In other embodiments, the registration of step 460 allows the probe position and/or trajectory can be mapped onto a virtual or true image of the overall anatomy (e.g., micro-tracking image 306 and/or macro tracking image 310 shown in FIG. 3g).

Once the true and virtual images are registered and a pose offset has been computed, the virtual image and the pose offset may be used to guide the catheter without use of the true images. For example, the use of the calculated a pose estimation and virtual probe location image may be useful to a clinician in guiding the probe and catheter through the anatomical passageways when the camera is removed or when the true vision images become obstructed by bodily materials such as blood or mucous. The pose estimation of the catheter may also be useful during procedures in which the image capture probe is removed and replaced by a therapeutic instrument such as a drug delivery device or an interventional instrument such as a biopsy device. Knowing the pose and trajectory of the catheter allows for greater precision when conducting further procedures through the catheter Although the registration systems and methods have been described herein with respect to teleoperated or hand operated interventional systems, these registration systems and methods will find application in a variety of medical and non-medical instruments in which accurate instrument image registration is required.

Although the systems and methods of this disclosure have been illustrated for use in the connected bronchial passageways of the lung, they are also suited for navigation and treatment of other tissues, via natural or surgically created connected passageways, in any of a variety of anatomical systems including the colon, the intestines, the kidneys, the brain, the heart, the circulatory system, or the like. The methods and embodiments of this disclosure are also suitable for non-interventional applications.

One or more elements in embodiments of the invention may be implemented in software to execute on a processor of a computer system such as control system 116. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, Intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method for using a flexible catheter in a medical procedure, the method being implemented using a processor and comprising:
    receiving an endoscopic image from a distal end of an endoscopic image capture probe positioned within an anatomic region;
    identifying a fiducial region in the endoscopic image;
    defining a subregion of a model of the anatomic region, the subregion corresponding to an area surrounding a measured position of the endoscopic image capture probe, the subregion including a first portion situated distally from the distal end of the endoscopic image capture probe and a second portion situated proximally from the distal end of the endoscopic image capture probe, the measured position of the endoscopic image capture probe being received from a sensor system included in the endoscopic image capture probe;
    identifying a search space defined by the subregion of the model, the search space including a plurality of virtual tissue structures from the subregion of the model;
    matching the fiducial region in the endoscopic image with a matched one of the plurality of virtual tissue structures in the subregion of the model of the anatomic region, wherein the matched one of the plurality of virtual tissue structures is associated with a virtual probe position;
    localizing a tip of the endoscopic image capture probe relative to the model of the anatomic region wherein localizing the tip includes determining an offset between the measured position of the endoscopic image capture probe and the virtual probe position; and
    guiding movement of the endoscopic image capture probe in the anatomic region based on the offset.

2. The method of claim 1 further comprising determining a virtual probe orientation of the tip of the endoscopic image capture probe from the matched one of the plurality of virtual tissue structures.

3. The method of claim 1 further comprising displaying the matched one of the plurality of virtual tissue structures from the model of the anatomic region.

4. The method of claim 1, wherein the subregion surrounding the measured position of the endoscopic image capture probe is defined by at least one of a sensor tolerance or an expected anatomic motion about the measured position of the endoscopic image capture probe relative to the anatomic region.

5. The method of claim 1, wherein matching the fiducial region further comprises:
    identifying one or more structural aspects of the fiducial region; and
    identifying a subset of the plurality of virtual tissue structures,
    wherein the subset of the plurality of virtual tissue structures includes the one or more structural aspects of the fiducial region.

6. The method of claim 5, wherein the fiducial region includes one or more lumens, and the one or more structural aspects includes at least one of lumen location, lumen orientation, lumen dimension, lumen contour, lumen anatomical label, and lumen shape.

7. The method of claim 5, wherein matching the fiducial region further comprises:
    calculating an optimum similarity measure for each of the plurality of virtual tissue structures in the subset; and selecting the matched one of the plurality of virtual tissue structures by identifying one of the plurality of virtual tissue structures in the subset exhibiting the optimum similarity measure.

8. The method of claim 7, wherein calculating the optimum similarity measure comprises:
iteratively rendering a plurality of views for each of the plurality of virtual tissue structures in the subset of the plurality of virtual tissue structures;
generating a plurality of interim similarity measures; and
selecting the optimum similarity measure from the plurality of interim similarity measures for each of the plurality of virtual tissue structures in the subset, the optimum similarity measure indicating a match to the fiducial region for the plurality of views.

9. The method of claim 1, further comprising registering the model of the anatomic region with the endoscopic image based on the localization of the tip of the endoscopic image capture probe.

10. The method of claim 1 further comprising:
removing the endoscopic image capture probe from a catheter body positioned within the anatomic region; and
inserting a tracked interventional instrument through the catheter body to conduct a procedure.

11. The method of claim 1, wherein the anatomic region comprises a lung.

12. A medical system comprising:
a flexible catheter sized to receive an image capture probe wherein the image capture probe is sized to extend within an anatomic region;
a sensor system; and
a processor configured to:
generate a model of the anatomic region, the model being three-dimensional;
receive an image from the image capture probe positioned within the anatomic region;
identify a fiducial region in the image received from the image capture probe;
define a subregion of the model corresponding to a three-dimensional area surrounding a measured position of the image capture probe, the measured position being received from the sensor system;
identify a search space defined by the subregion of the model to identify a plurality of virtual tissue structures in the subregion of the model of the anatomic region;
match a matched one of the plurality of the virtual tissue structures in the subregion of the model with the identified fiducial region in the image received from the image capture probe, wherein the matched one of the plurality of the virtual tissue structures is associated with a virtual probe position;
localize a tip of the image capture probe relative to the model of the anatomic region including determining an offset between the measured position of the image capture probe and the virtual probe position; and
guide movement of the image capture probe in the anatomic region based on the offset.

13. The medical system of claim 12 wherein the processor is further configured to determine a virtual probe orientation of the tip of the image capture probe from the matched one of the plurality of virtual tissue structures.

14. The medical system of claim 12, wherein the processor is further configured to generate a display of the matched one of the plurality of virtual tissue structures from the model of the anatomic region.

15. The medical system of claim 12, wherein the processor is further configured to
identify structural aspects of the fiducial region; and
identify a subset of the plurality of virtual tissue structures matching the structural aspects of the fiducial region.

16. The medical system of claim 15, wherein the processor is further configured to
perform an iterative rendering of each of the plurality of virtual tissue structures in the subset to match the fiducial region; and
identify a matched one of the plurality of virtual tissue structures based on the iterative rendering.

17. The medical system of claim 12, wherein the processor is further configured to register the model of the anatomic region to the image based on the localizing of the tip of the image capture probe.

18. The medical system of claim 17, further comprising a display system to display a rendering of the matched one of the plurality of virtual tissue structures based on the localizing of the tip of the image capture probe.

19. The medical system of claim 12, further comprising:
a steering system for steering a distal region of the flexible catheter, wherein the flexible catheter controls a probe pose; and
a control system for maintaining a catheter pose of the flexible catheter when the image capture probe is removed.

20. The medical system of claim 12, further comprising:
a flexible catheter sized to receive the image capture probe;
a steering system for steering a distal region of the flexible catheter, wherein the flexible catheter controls a probe pose; and
a tracked tool deployed through the flexible catheter, wherein the tracked tool is controlled by reference to a displayed virtual visualization image.

21. A method for using a flexible catheter in a medical procedure, the method comprising:
receiving a model of an anatomic region within a patient;
receiving an endoscopic image from an endoscopic image capture probe positioned within the anatomic region;
identifying a bifurcation structure in the endoscopic image;
defining a model subregion contained within the model of the anatomic region, the model subregion corresponding to an area surrounding a measured position of the endoscopic image capture probe received from a sensor system included in the endoscopic image capture probe;
identifying a search space defined by the model subregion of the model, the search space including a plurality of virtual bifurcation structures from the model subregion of the model;
matching the bifurcation structure in the endoscopic image with a matched one of the plurality of virtual bifurcation structures in the model subregion, wherein the matched one of the plurality of virtual bifurcation structures is associated with a virtual probe position;
determining an offset between the measured position of the endoscopic image capture probe and the virtual probe position; and
guiding movement of the endoscopic image capture probe in the anatomic region based on the offset.

* * * * *